United States Patent [19]

Dunbar et al.

[11] 4,281,118

[45] Jul. 28, 1981

[54] AMINOALKYLSULFIDES, AMINOALKYLSULFOXIDES, AND AMINOALKYLSULFONES

[75] Inventors: Joseph E. Dunbar; Louis E. Begin, both of Midland, Mich.

[73] Assignee: The Dow Chemical Company, Midland, Mich.

[21] Appl. No.: 49,029

[22] Filed: Jun. 18, 1979

[51] Int. Cl.³ ............... C07D 413/12; C07D 295/08; A61K 31/535; A61K 31/445

[52] U.S. Cl. ..................... 544/85; 544/129; 544/141; 544/159; 546/121; 546/208; 546/232; 260/326.5 S; 260/326.5 SF; 260/326.84; 424/248.52; 424/267; 424/274; 424/330; 564/341

[58] Field of Search ........................ 544/85

[56] References Cited

U.S. PATENT DOCUMENTS

| 2,659,756 | 11/1953 | Häfliger et al. | 260/567.6 |
| 4,134,996 | 1/1979 | Dunbar et al. | 424/330 |
| 4,141,983 | 2/1979 | Dunbar et al. | 424/267 |
| 4,155,907 | 5/1979 | Dunbar et al. | 424/248.5 |

FOREIGN PATENT DOCUMENTS 865063 9/1978 Belgium.

OTHER PUBLICATIONS

Allingham et al., Israel Journal of Chemistry, vol. 9, pp. 583–587 (1971).

*Primary Examiner*—Mark L. Berch

[57] ABSTRACT

Novel aminoalkylsulfides, aminoalkylsulfoxides and aminoalkylsulfones of the general formula

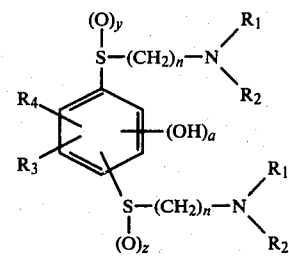

wherein y and z independently represent the integer 0, 1 or 2; a represents the integer 0 or 2; n represents the integer 1, 2, 3 or 4; $R_1$ independently represent lower alkyl or hydrogen or alternatively $R_1$ and $R_2$ taken together with the adjacent nitrogen atom represent a 5 or 6 membered heterocyclic ring which may optionally contain an oxygen atom whereby a morpholino, piperidino, or pyrrolidino grouping is formed; $R_3$ represents halo such as chloro or bromo, lower alkylthio, arlower-alkylthio, arylthio such as 4-methylphenylthio, 4-morpholinylloweralkylthio such as 4-morpholinylpropylthio, lower alkyl or arloweralkylamino such as 4-methoxybenzenemethanamino; $R_4$ represents hydrogen or lower alkyl. The invention also includes the pharmaceutically-acceptable salts of the compounds described herein.

8 Claims, No Drawings

AMINOALKYLSULFIDES, AMINOALKYLSULFOXIDES, AND AMINOALKYLSULFONES

BACKGROUND OF THE INVENTION

Adenosine diphosphate, hereafter called ADP, is a principal factor in the aggregation of blood platelets. Platelet aggregation in a mammal's bloodstream can result in the formation of a thrombus. Agents which interfere with ADP-induced blood platelet aggregation are of use as antithrombotic drugs.

SUMMARY OF THE INVENTION

The present invention relates to novel compounds of the general formula

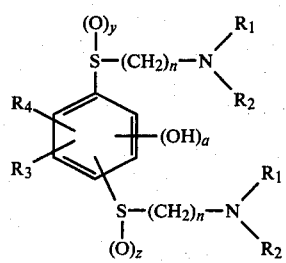

wherein y and z independently represent the integer 0, 1 or 2; a represents the integer 0 or 2; n represents the integer 1, 2, 3 or 4; $R_1$ and $R_2$ independently represent lower alkyl or hydrogen or alternatively $R_1$ and $R_2$ taken together with the adjacent nitrogen atom represent a 5 or 6 membered heterocyclic ring which may optionally contain an oxygen atom whereby a morpholino, piperidino, or pyrrolidino grouping is formed; $R_3$ represents halo such as chloro or bromo, lower alkylthio, arloweralkylthio, arylthio such as 4-methylphenylthio, 4-morpholinylloweralkylthio such as 4-morpholinylpropylthio, lower alkyl or arloweralkylamino such as 4-methoxybenzenemethanamino; $R_4$ represents hydrogen or lower alkyl. The invention also includes the pharmaceutically-acceptable salts of the compounds described herein.

As used in the specification and claims, the term lower alkyl refers to an alkyl group having from 1 to 4 carbon atoms such as a methyl, ethyl, propyl, isopropyl, butyl, isobutyl, or sec-butyl group; aryl refers to an unsaturated cyclic moiety usually phenyl or tolyl; and the term "pharmaceutically-acceptable salts" refers to non-toxic acid addition salts of the compounds, the anions of whih are relatively innocuous to animals at dosages consistent with good platelet aggregation inhibition so that the beneficial effects of the free base are not vitiated by the side effects ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids.

Compounds falling within the scope of this invention are useful for the inhibition of blood platelet aggregation or as anti-depressants in mammals.

DETAILED DESCRIPTION OF THE INVENTION

Compounds falling within the scope of the present invention may be prepared as follows: A benzenedithiol or substituted benzenedithiol of the general formula

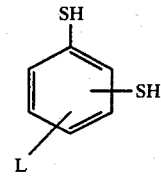

wherein L is halo or lower alkyl of from 1 to about 4 carbon atoms, is reacted with a substituted lower alkane, usually a disubstituted lower alkane or salt thereof. The substituted or disubstituted lower alkane is generally composed of from 1 to about 4 carbon atoms and the salt used generally is derived from mineral acids such as hydrochloric or sulfuric acids.

The substituted lower alkane has the general formula

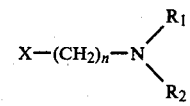

wherein X is a halogen moiety, preferably a chloro; wherein $R_1$, $R_2$ and n have the same meanings as defined above, to produce compounds with the general formula illustrated by Formula IV (below) or their pharmaceutically-acceptable salts wherein L, $R_1$, $R_2$, n and pharmaceutically-acceptable salts have the previously defined meanings.

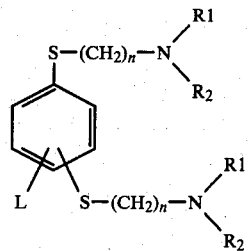

The formation of Formula IV compounds or their pharmaceutically-acceptable salts is illustrated by, but not limited to, Examples 1, 3, 5 and 10 herein.

Sulfides corresponding to Formula IV above can be oxidized to form sulfinyl and sulfonyl derivatives by oxidizing the sulfur with an oxidizing agent such as hydrogen peroxide. The production of the oxidized variants of Formula IV or their pharmaceutically-acceptable salts is illustrated by, but not limited to, Examples 2, 4, 8 and 11 herein. Oxidation products may contain both the sulfinyl and sulfonyl moieties as illustrated by Example 8 herein.

Additional derivatives can be prepared from the compounds represented by Formula IV by substituting for substituent L when it is a chloro or bromo. The moieties which are substituted for the chloro or bromo are defined by $R_3$ of Formula I. These substitutions are illustrated by, but not limited to, Examples 6, 7 and 9 herein.

Other derivatives can be formed by reacting a dialkylbenzoquinone in which the alkyl groups are from 1 to about 4 carbon atoms with a substituted aminoalkylthiol or salt thereof where the alkyl group is from 1 to about 4 carbon atoms and the salt is generally a salt of a mineral acid such as hydrochloric or sulfuric acid to form the dihydroxyl dialkyl derivatives of Formula I or their pharmaceutically-acceptable salts.

The above reaction is illustrated by, but not limited to, Example 12 herein.

EXAMPLE 1

Preparation of
4,4'-((4-chloro-1,3-phenylene)bis(thio-2,1-ethanediyl))bismorpholine bis(methanesulfonate)

To a solution of 22.2 grams (0.555 mole) of sodium hydroxide in 140 milliliters of water was added 31.0 grams (0.175 mole) of 4-chloro-m-benzenedithiol. To the resulting solution 70.7 grams (0.380 mole) of 4-(2-chloro-ethyl)morpholine hydrochloride was added and the reaction mixture was warmed to 75° C. with stirring and allowed to cool to room temperature. The mixture was then diluted with an equal volume of water and extracted with methylene chloride. The extract was dried over anhydrous sodium sulfate, and the solvent was removed by evaporation. The residue was dissolved in a minimum amount of absolute ethanol, and the solution was combined with a solution of an excess of methanesulphonic acid in absolute ethanol. The product, 4,4'-((4-chloro-1,3-phenylene)bis(thio-2,1-ethanediyl))bismorpholine bis(methanesulfonate) crystallized as a white solid, m.p. 201°-203° C., and was collected on a filter and dried.

Elemental analysis showed carbon 40.5%, hydrogen 5.82% and nitrogen 4.88% as compared to theoretical values of carbon 40.35%, hydrogen 5.93%, and nitrogen 4.71%.

EXAMPLE 2

Preparation of
4,4'-((4-chloro-1,3-phenylene)bis(sulfonyl-2,1-ethanediyl))bismorpholine dihydrochloride A solution of 10.0 g (0.0168 mole) of 4,4'-((4-chloro-1,3-phenylene)-bis(thio-2,1-ethanediyl)bismorpholine bis(methanesulfonate) and 8.0 g (0.071 mole) of 30% hydrogen peroxide in 50 ml of glacial acetic acid was warmed at 70° C. for five hours. The solvent was then removed by evaporation in vacuo, and the residue was dissolved in water. A small amount of insoluble substance was removed by filtration. The solution was made basic by the addition of 20% sodium hydroxide solution, and the mixture was extracted with methylene chloride. The extract was dried over anhydrous magnesium sulfate, filtered, and the solvent removed by evaporation. The residue was dissolved in absolute ethanol, and the solution acidified with ethanolic hydrogen chloride, resulting in the precipitation of the product, 4,4'-((4-chloro-1,3-phenylene)bis(sulfonyl-2,1-ethanediyl))bismorpholine dihydrochloride as a white, crystalline solid, m.p. 205°-206° C. The product was collected on a filter and dried.

Elemental analysis showed carbon 40.2%, hydrogen 5.49% and nitrogen 5.26% as compared to theoretical values of carbon 40.04%, hydrogen 5.41%, and nitrogen 5.19%.

EXAMPLE 3

Preparation of
4,4'-((4-chloro-1,3-phenylene)bis(thio-3,1-propanediyl))bismorpholine bis(4-methylbenzenesulfonate)

A stirred mixture of 50.0 g (0.283 mole) of 4-chloro-m-benzenedithiol, 92.6 g (0.566 mole) of 4-(3-chloropropyl)morpholine and a solution of 22.9 g (0.573 mole) of sodium hydroxide in 300 ml of water was warmed at from 60° to 65° C. for two hours, cooled and extracted with methylene chloride. The extract was dried over anhydrous sodium sulfate, and the solvent was removed by evaporation. The residue was dissolved in 500 ml of propanol-2, and the solution was combined with a propanol-2 solution of 102 g (0.536 mole) of p-toluenesulfonic acid monohydrate to give white crystals, m.p. 184.5°-185.5° C. This material was recrystallized from methanol to give the product, 4,4'-((4-chloro-1,3-phenylene)bis(thio-3,1-propanediyl)bismorpholine bis(4-methylbenzenesulfonte), as a white, crystalline solid, m.p. 186°-187° C.

Elemental analysis showed carbon 52.7%, hydrogen 6.12%, and nitrogen 3.85% compared to theoretical values of carbon 52.66%, hydrogen 6.11%, and nitrogen 3.61%.

EXAMPLE 4

Preparation of
4,4'-((4-chloro-1,3-phenylene)bis(sulfonyl-3,1-propanediyl))bismorpholine bis(4-methylbenzenesulfonate)

To a stirred suspension of 163 g (0.210 mole) of 4,4'-((4-chloro-1,3-phenylene)bis(thio-3,1-propanediyl)bismorpholine bis(4-methylbenzenesulfonate) in 600 ml of glacial acetic acid was added 94.5 g (0.834 mole) of 30% hydrogen peroxide over a period of 15 minutes, keeping the temperature below 36° C. by means of a water bath. When the addition was complete, total dissolution had occurred, and stirring was continued without the cooling bath for 30 minutes, after which period of time heat was applied, and the reaction mixture was maintained between 55° and 65° C. for an additional five hours. The solution was then stirred at room temperature for a period of 15 hours, and the solvent was removed by evaporation in vacuo. The residue was dissolved in water, and the pH was adjusted to 8.0 by addition of 20% sodium hydroxide solution. The mixture was extracted with methylene chloride, and the extract was dried over anhydrous sodium sulfate, filtered and evaporated to dryness. The residue was dissolved in a minimum of warm propanol-2 and the solution combined with a propanol-2 solution of two equivalents of p-toluenesulfonic acid monohydrate. The solution was cooled, and the resulting white, crystalline product, 4,4'-((4-chloro-1,3-phenylene)bis(sulfonyl-3,1-propanediyl))bismorpholine bis(4-methylbenzenesulfonate), m.p. 231°-233° C., was collected on a filter and dried. Recrystallization from propanol-2-water (5:1) gave the pure crystalline substance, m.p. 232°-234° C.

Elemental analysis showed carbon 48.9%, hydrogen 5.64% and nitrogen 3.48% as compared to theoretical values of carbon 48.64%, hydrogen 5.64% and nitrogen 3.34%.

EXAMPLE 5

Preparation of
4,4'-((4-methyl-1,2-phenylene)bis(thio-3,1-propanediyl))bismorpholine dihydrochloride To a warm (60° C.) solution of 10.0 g (0.0640 mole) of 4-methyl-o-benzenedithiol, 5.12 g (0.128 mole) of sodium hydroxide in 70 ml of water was added 21.0 g (0.128 mole) of 4-(3-chloropropyl)morpholine. The reaction mixture was stirred at 60° to 65° C. for 30 minutes, cooled and extracted with methylene chloride. After the extract was dried over anhydrous magnesium sulfate and filtered, ethanolic hydrogen chloride was added, and the solvent and excess hydrogen chloride were removed by evaporation in vacuo. The oily residue was crystallized from propanol-2. Recrystallization from methanol-propanol-2 (1.4:1) gave the product, 4,4'-((4-methyl-1,2-phenylene)bis(thio-3,1-propanediyl))bismorpholine dihydrochloride as white crystals, m.p. 233–234° C.

Elemental analysis showed carbon 52.5%, hydrogen 7.53% and nitrogen 6.11% as compared to theoretical values of carbon 52.26%, hydrogen 7.52% and nitrogen 5.81%.

EXAMPLE 6

Preparation of
4,4'-((4-((4-methylphenyl)thio)-1,3-phenylene)bis(sulfonyl-3,1-propanediyl))bismorpholine
bis(4-methylbenzenesulfonate)

A stirred mixture of 10.0 g (0.0119 mole) of 4,4'-((4-chloro-1,3-phenylene)bis(sulfonyl-3,1-propanediyl))bismorpholine bis(4-methylbenzenesulfonate), 1.6 g (0.012 mole) of 90% p-thiocresol and 1.5 g (0.038 mole) of sodium hydroxide in 55 ml of water was warmed for 30 minutes at 65° to 70° C., during which time the crude product separated as a hard gum. The aqueous phase was decanted, and the gum was dissolved in a minimum of warm propanol-2. This solution was treated with a propanol-2 solution of an excess of p-toluenesulfonic acid monohydrate. On cooling, the solution yielded a crystalline product. Recrystallization from propanol-2 gave the pure product, 4,4'-((4-((4-methylphenyl)thio)-1,3-phenylene)bis(sulfonyl-3,1-propanediyl))bismorpholine bis(4-methylbenzenesulfonate), as buff crystals, m.p. 215.5°–216.5° C.

Elemental analysis showed carbon 53.0%, hydrogen 5.87% and nitrogen 3.20% compared to theoretical values of carbon 53.11%, hydrogen 5.87% and nitrogen 3.02%.

EXAMPLE 7

Preparation of
N-(2,4-bis((3-(4-morpholinyl)propyl)sulfonyl)phenyl)-4-methoxybenzenemethanamine A solution, consisting of 10.0 g (0.0119 mole) of 4,4'-((4-chloro-1,3-phenylene)bis(sulfonyl-3,1-propanediyl))bismorpholine bis(4-methylbenzenesulfonate), 1.7 g (0.012 mole) of p-methoxybenzylamine and 3.7 g (0.037 mole) of triethylamine in 100 ml of ethanol, was heated under reflux for 18 hours. The ethanol was then removed by evaporation in vacuo, and the residual substance was dissolved in 85 ml of water. Enough 20% sodium hydroxide solution was added to cause precipitation of the crude free base as an amber liquid. This was extracted with methylene chloride, the extract dried over anhydrous sodium sulfate, and the solvent removed by evaporation in vacuo, leaving a brown, viscous oil. The oil was dissolved in a minimum of boiling ethanol, and the resulting solution was treated with activated charcoal and filtered while hot. The filtrate was cooled to give the product, N-(2,4-bis(3-(4-morpholinyl)propyl)sulfonyl)phenyl)-4-methoxybenzenemethanamine, as white crystals, mp. 121°–122° C.

Elemental analysis showed carbon 56.6%, hydrogen 7.06% and nitrogen 6.79% compared to theoretical values of carbon 56.45%, hydrogen 6.94% and nitrogen 7.05%.

EXAMPLE 8

Preparation of
4-(3-((2-chloro-5-(3-((4-morpholinyl)propyl)sulfonyl)-phenyl)sulfinyl)propyl)morpholine
bis(4-methylbenzenesulfonate)

30% Hydrogen peroxide (11.9 g, 0.105 mole) was added slowly to a solution of 38.8 g (0.0500 mole) of 4,4'-((4-chloro-1,3-phenylene)bis)thio-3,1-propanediyl))bismorpholine bis(4-methylbenzenesulfonate) in 150 ml of glacial acetic acid with stirring, keeping the temperature of the reaction mixture below 35° C. The solution was then heated on the steam bath at from 75° to 90° C. for a period of two hours, cooled and allowed to stand at ambient temperature for 15 hours. Toluene was then added to the reaction mixture to serve as an azeotroping agent, and the combined solvents were removed by evaporation in vacuo, leaving a pale yellow, viscous oil. The oil was crystallized from a mixture of ethanol and methanol to give a white, crystalline solid, mp 183° C. A second recrystallization from ethanol-methanol gave the pure product, 4-(3-((2-chloro-5-(3-((4-morpholinyl)propyl)sulfonyl)phenyl)sulfinyl)propyl)morpholine bis(4-methylbenzenesulfonate), mp 187.5°–188° C.

Elemental analysis showed carbon 49.5%, hydrogen 5.80% and nitrogen 3.44% compared to theoretical values of carbon 49.59%, hydrogen 5.75%, and nitrogen 3.40%.

EXAMPLE 9

Preparation of
4,4'-((4-((3-(4-morpholinyl)propyl)thio)-1,3-phenylene)-bis(sulfonyl-3,1-propanediyl))bismorpholine A solution of 5.0 g (0.0060 mole) of 4,4'-((4-chloro-1,3-phenylene)bis(sulfonyl-3,1-propanediyl))bismorpholine bis(4-methylbenzenesulfonate), 1.4 g (0.0060 mole) of S-(3-(4-morpholinyl)propyl)isothiourea hydrochloride and 0.8 g (0.02 mole) of sodium hydroxide in 80 ml of water was heated under reflux with stirring for 3.5 hours, cooled and extracted with methylene chloride. The extract was dried over anhydrous sodium sulfate, and the solvent was removed by evaporation, leaving the product as 4,4'-((4-((3-(4-morpholinyl)propyl)thio)-1,3-phenylene)bis(sulfonyl-3,1-propanediyl))bismorpholine a yellow, viscous oil.

Elemental analysis showed carbon 52.0%, hydrogen 7.58% and nitrogen 7.03% as compared to theoretical values of carbon 52.31%, hydrogen 7.32% and nitrogen 6.78%. NMR (CDCl$_3$) δ8.49 (d, 1, J=1 Hz, arom. H between SO$_2$ grps.), 8.05 (d, 1, J=4 Hz, arom. H ortho to —S—), 7.64 (d, 1, J=4 Hz, arom. H meta to SO$_2$ grps.), 3.9–2.9 (m, 18, (O(CH$_2$)$_2$)$_3$, S—CH$_2$, (SO$_2$CH$_2$)$_2$) and 3.9–1.4 ppm (m, 24, (((CH$_2$)$_2$—NCH$_2$CH$_2$)$_3$).

EXAMPLE 10

Preparation of 3,3'-((4-chloro-1,3-phenylene)bis(thio))bis(N,N-dimethyl-1-propanamine) bis(4-methylbenzenesulfonate)

A stirred mixture of 8.0 g (0.045 mole) of 4-chloro-m-benzenedithiol, 16.0 g (0.101 mole) of 3-(dimethylamino)propyl chloride hydrochloride and 27.6 g (0.200 mole) of anhydrous potassium carbonate in 250 ml of dimethylformamide was warmed at 70° C. for 2.5 hours, cooled, diluted with water and extracted with methylene chloride. The extract was dried over anhydrous magnesium sulfate, filtered and the solvent removed by evaporation. The residue was dissolved in propanol-2, and this solution was treated with a propanol-2 solution of 38.0 g (0.200 mole) of p-toluenesulfonic acid monohydrate. The resulting precipitate was recrystallized from dimethylformamide to give the product, 3,3'-((4-chloro-1,3-phenylene)bis(thio))bis(N,N-dimethyl-1-propanamine) bis(4-methylbenzenesulfonate) as a white, crystalline solid, mp 146.5°-147.5° C.

Elemental analysis showed carbon 52.0%, hydrogen 6.12% and nitrogen 4.22% as compared to theoretical values of carbon 52.11%, hydrogen 6.27% and nitrogen 4.05%.

EXAMPLE 11

Preparation of 3,3'-((4-chloro-1,3-phenylene)bis(sulfonyl)bis(N,N-dimethyl-1-propanamine) bis(4-methylbenzenesulfonate)

A solution of 10.0 g (0.0145 mole) of 3,3'-((4-chloro-1,3-phenylene)bis(thio)bis(N,N-dimethyl-1-propanamine) bis(4-methylbenzenesulfonate) and 6.5 g (0.057 mole) of 30% hydrogen peroxide was warmed at 50° C. for 15 hours. The solution was then heated to 100° C. over a period of 45 minutes to complete the reaction. The major portion of the acetic acid was removed by evaporation in vacuo, and the residue was made alkaline by the addition of an appropriate amount of 20% sodium hydroxide solution. The mixture was extracted with methylene chloride, and the extract was dried over anhydrous sodium sulfate followed by the removal of the solvent by evaporation. The residue (6.5 g) was combined with a propanol-2 solution of 6.6 g (0.034 mole) of p-toluenesulfonic acid monohydrate to give a solid precipitate, mp 194°-196° C. Recrystallization from a mixture of propanol-2 and methanol (1:1) gave the pure product, 3,3'-((4-chloro-1,3-phenylene)bis(sulfonyl)bis(N,N-dimethyl-1-propanamine) bis(4-methylbenzenesulfonate), as a white, crystalline solid, mp 196.5°-197.5° C.

Elemental analysis showed carbon 47.41%, hydrogen 5.84% and nitrogen 3.89% as compared to theoretical values of carbon 47.70%, hydrogen 5.74% and nitrogen 3.71%.

EXAMPLE 12

Preparation of 2,5-bis((3-(dimethylamino)propyl)thio)-3,6-dimethyl-1,4-benzenediol dihydrochloride A mixture of 27.2 g (0.200 mole) of 2,5-dimethyl-1,4-benzoquinone, 31.1 g (0.200 mole) of 3-(dimethylamino)propanethiol hydrochloride and six drops of triethylamine in 300 ml of acetone was stirred at ambient temperature for 15 hours. The cream-colored, crude, solid product was collected on a filter and recrystallized from methanol to give the pure product, 2,5-bis((3-(dimethylamino)propyl)thio)-3,6-dimethyl-1,4-benzenediol dihydrochloride, as cream-colored platelets, mp 254.5° C.

Elemental analysis showed carbon 48.2%, hydrogen 7.52% and nitrogen 6.24% as compared to theoretical values of carbon 48.52%, hydrogen 7.69% and nitrogen 6.29%.

The NMR spectrum showed no absorption in the aromatic region.

The compounds identified in Examples 1, 2, 3, 4, 5, 8, 9, 10, 11 and 12 showed IC$_{50}$ values ranging from about 0.002 to about 6 μm/ml for ADP. The effective blood platelet aggregation inhibiting amount of the compounds of the invention to be administered internally to a mammal, that is the amount which is effective to substantially inhibit the aggregation of blood platelets in the presence of ADP, can vary depending upon such factors as the animal treated, the particular compound administered, the period of administration, and the method of administration.

Although the compounds 4,4'-((4-((4-methylphenyl)-thio)-1,3-phenylene)bis(sulfonyl-3,1-propanediyl))bis-morpholine bis(4-methylbenzenesulfonate), described in Example 6 herein and N-(2,4-bis((3-(4-morpholinyl)propyl) sulfonyl)phenyl)-4-methoxybenzenemethanamine described in Example 7 herein have not demonstrated antithrombotic activity they have been shown to be anti-depressants.

Platelet aggregation was demonstrated by techniques originally described by Born in *Nature* 194, 927 (1962). Using this technique, platelet aggregation was initiated in platelet rich plasma by 0.0625-1.0 μg/ml of ADP. Rat blood was collected into a 3.0% sodium citrate solution by cardiac puncture under methoxyfurane anesthesia. The blood was centrifuged at 120X g for about 10 minutes at room temperature and the supernatant platelet rich plasma was removed and diluted with lactated Ringer's solution containing the inhibitory agent. Samples of 1.0 ml were pipetted into plastic-test tubes and incubated at 37° C. for ten minutes. Platelet aggregation in response to the ADP challenge was measured on a Chrono-Log Aggregometer at 37° C. The concentration that produced 50% of the maximum response for each agent (IC$_{50}$) was established by determining a concentration-response relationship by linear regression analysis.

What is claimed:

1. A compound of the formula

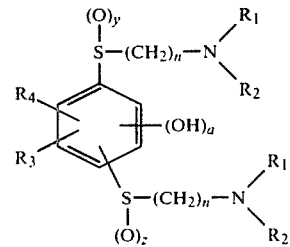

wherein y and z independently represent the integer 0, 1 or 2; a represents the integer 0; n represents the integer 1, 2, 3 or 4; R$_1$ and R$_2$ taken together with the adjacent nitrogen atom represent morpholino; R$_3$ represents halo, 4-morpholinylloweralkylthio, or lower alkyl; R$_4$ represents hydrogen and further including the pharmaceutically-acceptable salts thereof.

2. The compound of claim 1 which is 4,4'-((4-chloro-1,3-phenylene)bis(thio-2,1-ethanediyl))bismorpholine or a pharmaceutically-acceptable salt thereof.

3. The compound of claim 1 which is 4,4'-((4-chloro-1,3-phenylene)bis(sulfonyl-2,1-ethanediyl))bismorpholine or a pharmaceutically-acceptable salt thereof.

4. The compound of claim 1 which is 4,4'-((4-chloro-1,3-phenylene)bis(thio-3,1-propanediyl))bismorpholine or a pharmaceutically-acceptable salt thereof.

5. The compound of claim 1 which is 4,4'-((4-chloro-1,3-phenylene)bis(sulfonyl-3,1-propanediyl))bismorpholine or a pharmaceutically-acceptable salt thereof.

6. The compound of claim 1 which is 4,4'-((4-methyl-1,2-phenylene)bis(thio-3,1-propanediyl))bismorpholine or a pharmaceutically-acceptable salt thereof.

7. The compound of claim 1 which is 4-(3-((2-chloro-5-(3-((4-morpholinyl)propyl(sulfonyl)phenyl)sulfinyl)propyl)morpholine or a pharmaceutically-acceptable salt thereof.

8. The compound of claim 1 which is 4,4'-((4-((3-(4-morpholinyl)propyl)thio)-1,3-phenylene)bis(sulfonyl-3,1-propanediyl))bismorpholine or a pharmaceutically-acceptable salt thereof.

* * * * *